United States Patent [19]

Johnson et al.

[11] Patent Number: 4,885,207

[45] Date of Patent: Dec. 5, 1989

[54] BIOCOMPATIBLE PROTEIN OR LIGAND IMMOBILIZATION SYSTEM

[75] Inventors: Susan S. Johnson, E. Forest Lake; James R. Goodman, Chicago, both of Ill.

[73] Assignee: UOP, Des Plaines, Ill.

[21] Appl. No.: 73,251

[22] Filed: Jul. 13, 1987

[51] Int. Cl.$^4$ .................. B32B 33/00; G01N 33/547
[52] U.S. Cl. ........................ 428/403; 428/407; 428/408; 428/688; 428/689; 435/180; 435/176; 436/524; 436/527; 436/531; 436/534; 436/85; 530/389; 530/403; 530/413; 530/815
[58] Field of Search .............. 428/403, 408, 688, 689, 428/407; 435/180, 176; 436/524, 527, 531, 534, 85; 530/389, 403, 413, 815

[56] References Cited

U.S. PATENT DOCUMENTS

| | | | |
|---|---|---|---|
| Re. 28,635 | 12/1975 | Youtsey et al. | 428/409 |
| 3,840,509 | 10/1974 | Youtsey et al. | 427/82 |
| 3,916,066 | 10/1975 | Youtsey et al. | 428/409 |
| 3,992,212 | 11/1976 | Youtsey et al. | 106/1 |
| 4,090,978 | 5/1978 | Welsh et al. | 252/425.3 |
| 4,193,910 | 3/1980 | Rohrbach et al. | 435/180 |
| 4,292,199 | 9/1981 | Rohrbach et al. | 435/180 |
| 4,336,161 | 6/1982 | Rosevear et al | 530/413 |
| 4,459,372 | 7/1984 | Arena | 502/351 |
| 4,536,358 | 8/1985 | Welsh et al. | 264/81 |
| 4,581,336 | 4/1986 | Malloy et al. | 435/180 |
| 4,753,983 | 6/1988 | Ngo | 435/180 |

OTHER PUBLICATIONS

Michael D. Klein and Robert Langer, *Trends in Biotech.*, Jul., 1986, pp. 179–186.

*Primary Examiner*—Robert Benson
*Attorney, Agent, or Firm*—Thomas K. McBride; Eugene I. Snyder

[57] ABSTRACT

A support matrix generally useful for the immobilization of biologically active proteins is made by coating with a polymeric alcohol a core support of titania or a carbonaceous pyropolymer deposited on a high surface area refractory inorganic oxide, cross-linking the alcohol, and converting a portion of the hydroxyl moieties to sulfonate esters. Such supports covalently bind enzymes and antibodies via a strong carbon-nitrogen single bond to give, for example, an immobilized antibody system extremely resistant to leaching of the antibody, the cross-linked alcohol, or of metals from the core support.

19 Claims, 1 Drawing Sheet

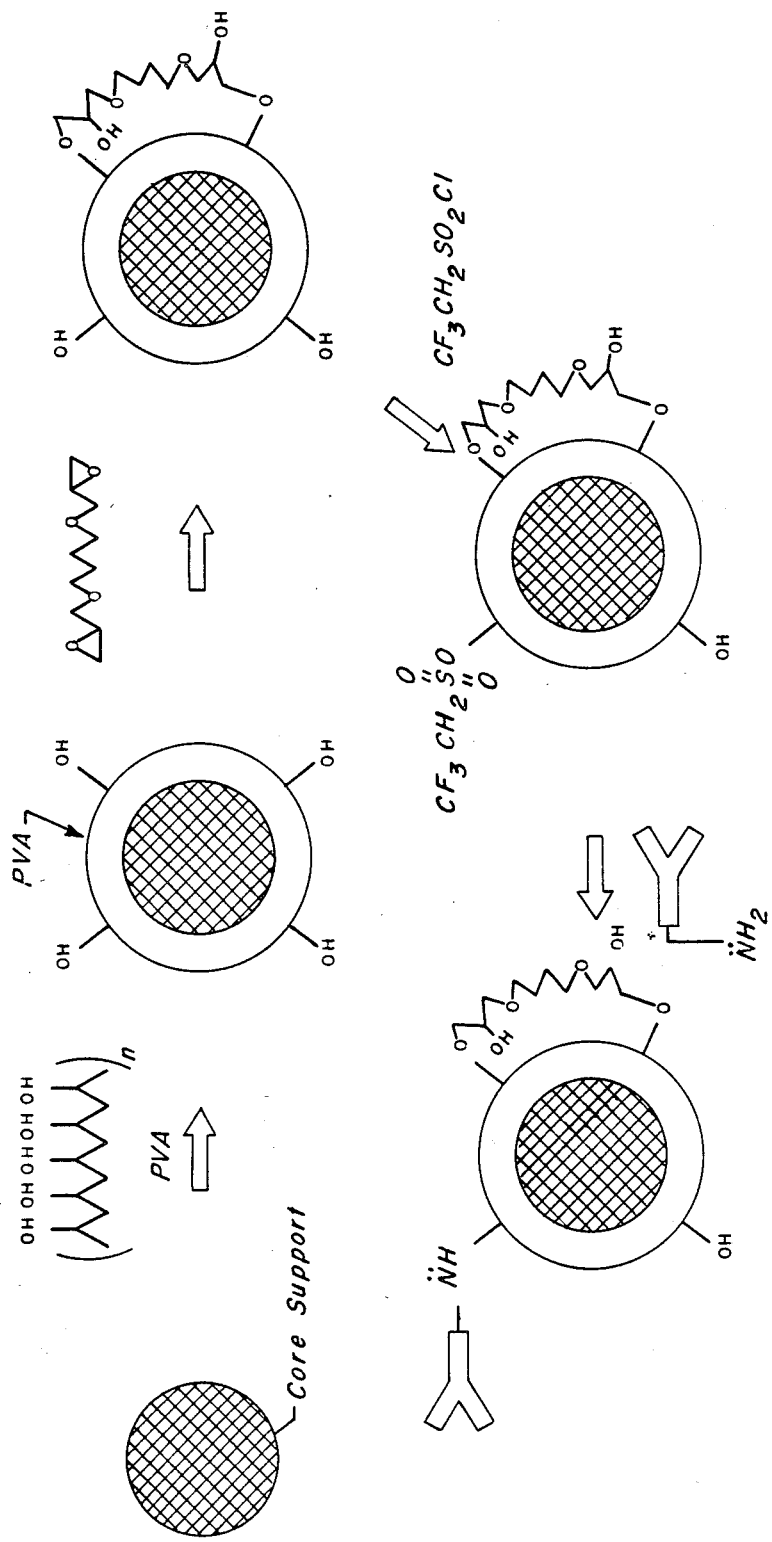

BIOCOMPATIBLE PROTEIN OR LIGAND IMMOBILIZATION SYSTEM

BACKGROUND OF THE INVENTION

Since approximately the early 70's a variety of support systems has been developed for the immobilization of biologically active proteins, especially enzymes. Some are based on ion exchange forces for immobilization of enzymes, others use physical entrapment of the enzyme, and still others are based on covalent bond formation between a functional group on the support matrix and one on the enzyme, the latter one usually being an amino group. Although such support systems are, in principle, suitable for all varieties of biologically active proteins, certain uses place stringent operational demands on a support, demands which the prior art materials are not designed to meet. This is particularly true for immobilized antibodies.

For example, immunoaffinity chromatography is an especially useful procedure for the purification of products from a fermentation broth. In particular, immunoaffinity chromatography is quite well suited for the isolation of extracellular material expressed by a microorganism as the result of recombinant DNA incorporated into it. In such cases the desired product is viewed as an antigen, and an immobilized antibody specific to the desired product selectively and efficiently removes it from the fermentation broth by forming an insoluble antibody-antigen complex firmly held on the column of solid support to which the antibody is immobilized. When all the product has been removed, or when the support approaches saturation with the antigen, the antigen is eluted from the column by breaking the antibody-antigen complex and releasing pure antigen into the eluant. With removal of the antigen the antibody is regenerated, and the column once more can be used for immunoaffinity chromatography.

Since antibody-antigen complexes typically are quite strong their cleavage to release the antigen requires elution with a reagent often found to be deleterious to the immobilized antibody system. That is, eluants used often are not benign and often cause chemical disruption of the immobilized antibody system which may be a disruption of either the underlying support or the bound antibody. Such eluants are exemplified by strong acids, strong bases, detergents, and chaiotropic reagents. The result is that the antibody or some component of the underlying support matrix leaches into the eluant and ultimately contaminates the antigen-containing products. The presence of such contaminants in the product can be especially detrimental in purifying injectable materials, or when immunoaffinity chromatography with a bound antibody or enzyme is used for extracorporeal blood treatments.

The requirements of a support for antibody immobilization can be simply stated. The system must be low leaching, both in the context of solubilization of the antibody and of all components of the underlying support matrix. Low leaching with respect to the antibody requires that the latter be immobilized via a strong covalent bond. Low leaching with respect to the underlying support matrix means that all components as a whole must be very resistant to harsh chemical conditions. Additionally, the support matrix for an immobilized antibody is desirably incompressible so that it can accommodate high flow rates when used in, for example, a fixed bed. Because the immobilized antibody often may be used to purify or selectively remove a protein, it is imperative that the immobilized system minimize non-specific adsorption of protein. That is, a protein not an antigen for an immobilized antibody should not be absorbed by the immobilized antibody system via general and non-specific adsorption by the remainder of the support matrix, else there is a likelihood of such proteins being subsequently eluted upon release of the antigen with contamination of the product. Finally, there is a pragmatic need to maximize antibody loading (concentration of antibody immobilized per unit weight of support matrix) for optimizing process efficiency.

Immobilized antibodies or enzymes can be used for extracorporeal blood treatment if the immobilization system is covalent such that an immune response is not generated and non-thrombogenic. The system must not be chemically or enzymatically degraded by blood nor must it cause hemolysis, thrombosis or platelet removal. It also should not be toxic nor carcinogenic. In addition, the support should have low compressibility and good flow properties. In extracorporeal treatment, the serum fraction of the patient's blood containing the anticoagulant heparin is passed directly over the immobilized protein. Enzymes such as asparaginase, bilirubin oxidase, phenylalanine ammonia lyase and heparinase have been somewhat successfully used to lower the serum concentrations of asparagine, bilirubin, phenylalanine and heparin, respectively, in animal models. M. D. Klein and R. Langer, *Trends in Biotech.*, July, 1986, p. 179–186.

We have found a new family of support matrices which exhibit such favorable characteristics. In a sense these may be viewed as second generation systems for immobilization of biologically active proteins because they represent a significant advance in the operational sense as described above. Such materials satisfy needs not envisaged when the prior art support matrices were designed simply because the needs arose from demands imposed by new uses.

DESCRIPTION OF THE FIGURE

FIG. 1 is a pictorial representation of an embodiment of the support matrix and immobilized antibody system, as well as a method of making them, according to the invention described within.

SUMMARY OF THE INVENTION

The purpose of this invention is to prepare a support matrix which is low leaching under harsh conditions, which is incompressible, to which a biologically active protein can be immobilized via covalent bonding with high loading, and which shows little non-specific adsorption of proteins. An embodiment is a support matrix of a core support to which is attached a polymeric polyol which is subsequently cross-linked with at least some of the remaining hydroxyl groups being converted to sulfonate esters. In a more specific embodiment the core support is a carbonaceous pyropolymer deposited on a refractory inorganic oxide and the polymeric polyol is polyvinyl alcohol. In a still more specific embodiment the polyvinyl alcohol is cross-linked by a diglycidyl ether. In a still more specific embodiment the sulfonate ester is a trifluoroethanesulfonate. Additional embodiments will become apparent from the following description.

DESCRIPTION OF THE INVENTION

The invention herein is a method of making a support matrix for the immobilization of biologically active proteins, especially antibodies, comprising coating a core support with a polymeric alcohol, cross-linking the alcohol by reacting an excess of an hydroxyl-reactive cross-linking agent with the coated polymeric alcohol, converting a portion of the hydroxyl groups of the cross-linked alcohol to a sulfonate ester, then recovering the resulting support matrix. In another aspect the invention herein is the support matrix arising by the foregoing method. In yet another aspect our invention is the immobilized enzyme or antibody system, and method of making same, where the underlying support matrix is as described previously.

The underlying rationale as well as a pictorial representation of the support matrix and immobilized antibody system resulting therefrom is depicted in FIG. 1. The core support is an incompressible solid which provides a structural framework for the remainder of the support matrix. The core support itself is chemically quite resistant to the harsh conditions which an immobilized antibody system may be exposed to. Thus, for example, the core support will itself be low leaching under extremes of pH, in the presence of chaiotropic reagents, and at high salt concentrations. Such chemical stability is also accompanied by a high physical stability so that the support will show high resistance to abrasion and attrition under normal conditions of use.

The core support alone provides insufficient means for immobilizing a biologically active protein via covalent bonding. Thus, the core support will be encased in an organic resin having reactive functional groups capable of covalently bonding to free amino groups of biologically active proteins. This resin, which is physically quite strongly attached to the core support and will itself be resistant to leaching, is a cross-linked polymeric alcohol which in the figure is polyvinyl alcohol. The polyvinyl alcohol coated core support is then cross-linked so as to provide strong adhesion to the core support. The cross-linking agent reacts with a multiplicity of hydroxyl groups on the coating and in essence forms a very highly cross-linked network on the core support.

The resulting resin still has a multiplicity of hydroxyl groups which are then converted, at leat in part, to sulfonate esters. Sulfonate esters as a class are known to be excellent leaving groups in nucleophilic substitution reactions, and primary amino groups as a class are known to be good nucleophiles in nucleophilic substitution reactions. Sulfonate esters are chosen which are particularly good leaving groups, and a portion of the hydroxyl groups of the cross-linked organic resin is then converted to such sulfonate esters. In the last sequence there is shown the nucleophilic displacement of the sulfonate group by a primary amino group of, for example, an antibody with formation of a strong nitrogen-carbon covalent bond which is very stable under conditions of use of the immobilized biologically active protein. We now will proceed to describe our invention in greater detail.

As previously stated, the core support should be noncompressible and very resistant to the harsh reagents often used as eluants in immunoaffinity chromatography. We have found that both titania and carbonaceous pyropolymers deposited on refractory inorganic oxides are especially suitable in the practice of our invention, although not necessarily with equivalent results. The latter core supports are from a class of carbonaceous pyropolymer which possesses recurring units containing at least carbon and hydrogen atoms deposited on a high surface area inorganic oxide. These materials are described in U.S. Pat. No. 4,536,358, and in Re Pat. No. 28,635, U.S. Pat. No. 3,916,066, U.S. Pat. No. 3,940,509, U.S. Pat. No. 3,992,212, and U.S. Pat. No. 4,090,978, all of which are completely incorporated by reference. Typically such material contains between about 7 to about 38 weight percent carbon although we do not intend this to mean that such a range is necessary for our invention to be operative. Rather, this is just a conveniently prepared sort of material.

Among the inorganic oxides on which the pyropolymer is deposited and which we have found to be especially suitable in the practice of this invention are alumina, silica alumina, silica, controlled pore glass, hydroxyapatite, zirconia, zirconia titania, and alumina zirconia. We prefer the use of alumina, especially a relatively high surface area alumina, and have found it quite convenient to use an alumina with a surface area on the order of about 150 $m^2/g$.

Both titania, and more particularly, titania-coated alumina (titanated alumina; see U.S. Pat. No. 4,459,372) also can be used in the practice of our invention, but not necessarily with equivalent results. Such materials should have a surface area contribution of more than about 6 $m^2/g$ arising from pores of greater than 300 Angstroms with a pore volume from pores larger than 300 Angstroms of greater than about 0.15 cc/g and from pores larger than 1,000 Angstroms of greater than 0.10 cc/g. In general, the greater the macroporosity, i.e., the pore volume contributed by pores larger than 300 Angstroms, the more desirable is the material.

The core support is then coated with a polymeric alcohol. Among the polymeric alcohols which can be used are included materials such as polyvinyl alcohol, agarose, and cellulose esters which are less than 100% esterified. In a practical sense, most cellulose esters have a substantial fraction of free hydroxyl groups and, even though they are designated as esters, can be used in the practice of this invention because they supply sufficient hydroxyl moieties to be operative.

We have found that polyvinyl alcohol is a superior kind of polymeric alcohol to employ in the practice of our invention. Molecular weights between about 2,000 and about 25,000 are preferred. Polyvinyl alcohol of higher molecular weight, through at least 100,000, also may be used in the practice of this invention, but such materials are less desirable since they tend to lead to greater non-specific protein adsorption than do the lower molecular weight polymers. Commercially, polyvinyl alcohol results from the hydrolysis of polyvinyl acetate with commercial polyvinyl alcohol representing a range of hydrolyzed material. We have found that the range between about 70 and 100% hydrolyzed material affords more or less equivalent results, and such materials seem to be able to be used interchangeably.

It is desired to have at least about 3 weight percent of polyvinyl alcohol on the support, preferably greater than about 7 weight percent with the range between about 7 and 15 weight percent preferred and that from about 7 to about 9 weight percent particularly preferred. As the amount of polyvinyl alcohol coating the core support increases up to about 7.5 weight percent it is found that non-specific protein adsorption tends to decrease. It also has been found that too high a level of polymeric alcohol coating, above about 9 percent, may tend to reduce somewhat the loading of enzyme on the final support matrix.

The core support coated with a polymeric alcohol is then reacted with an excess of a hydroxyl-reactive cross-linking agent so as to extensively cross-link the polymeric alcohol. Cross-linking is effected to increase the physical adhesion of the polymeric alcohol to the core support, thereby reducing leaching of the polymeric alcohol arising from physical attrition. Additionally, since such polymeric alcohols may show significant water solubility, extensive cross-linking reduces such solubility to an extent as to make leaching by solubilization virtually nonexistent.

One class of cross-linking agents which may be used are diglycidyl ethers having the formula,

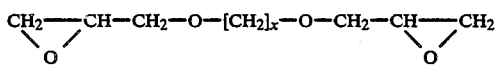

where x is an integer from 1 to 10, especially from 2 through 6. The diglycidyl ether from 1,4-butanediol is particularly recommended. When using glycidyl ethers to cross-link polyvinyl alcohol, from 2.5 to about 50 millimoles of glycidyl ether per gram of polyvinyl alcohol is recommended, which is equivalent of 0.11–2.2 molar proportions relative to the polyvinyl alcohol hydroxyl groups. A measure of cross-linking is afforded by gelling a solution of the polyvinyl alcohol. Gelling seems to be promoted by the presence of a borohydride, such as sodium borohydride or sodium cyanoborohydride, and appears to occur most readily in an aqueous alcohol containing more than about 20 volume percent of alcohol, with 40 volume percent alcohol being recommended. The alcohols which may be used include methanol, ethanol, 1-propanol, i-propyl alcohol, secondary and tertiary butyl alcohol under conditions where the latter are soluble to the requisite extent. Ethanol is by far the most convenient alcohol to use.

Other cross-linking agents also may be successfully used in the practice of our invention. Such cross-linking agents include epichlorohydrin, aliphatic diisocyanates of formula $OCN(CH_2)_yNCO$ where y is an integer from 2 through about 10, especially from 4 through about 8, aromatic diisocyanates such as benzene diisocyanate and toluene diisocyanate, and divinylsulfone. In all cases a large molar excess of cross-linking agent is used to ensure extensive cross-linking of the polymeric alcohol coating the core support.

At this stage one has prepared a cross-linked resin containing a multiplicity of hydroxyl moieties coating and firmly attached to a low leaching core support. What is desired is to transform the hydroxyl moiety to one which is a facile leaving group in a nucleophilic substitution. This is schematically represented by the equation,

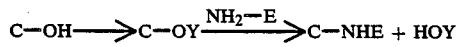

The moiety COY should be easy to prepare in high yield. The reagent furnishing Y should be not too expensive and easily available. The subsequent displacement of OY by $NH_2E$ should occur readily under mild conditions and in high yield. Finally, the grouping COY should not be a charged or polarized species. The reason for the latter requirement is that if the cross-linked resin is transformed into a charged or polarized species this leads to immobilization via ion exchange with subsequent leaching of the immobilized biological, and also leads to higher non-specific protein adsorption.

Sulfonate esters generally are known to be good leaving groups in nucleophilic substitution reactions, and we have found that when OY is a sulfonate ester its displacement by an amino group of an enzyme or antibody or other biologically active protein proceeds rather readily. The particular sulfonate esters which may be used are well known to the skilled practitioner since the area of nucleophilic substitution has been quite thoroughly investigated over the years. Illustrative of such sulfonate esters are the trifluoroethanesulfonate, trifluoromethanesulfonate, para-toluenesulfonate, para-bromobenzenesulfonate, 2,4-dinitrobenzenesulfonate, para-nitrobenzenesulfonate, and so on. The preparation of the sulfonate esters generally is accomplished by reaction of the resin with an activated sulfonic acid, usually a sulfonyl halide, generally a chloride although the fluoride and bromide also may be used. Reaction of the sulfonyl halide with the alcoholic resin takes place in the presence of a base of neutralize the acid formed in the reaction. In any event, the preparation of sulfonate esters is so well known that no more needs to be said about it.

The relative amount of hydroxylic groups on the cross-linked resin converted to sulfonate esters is susceptible to great variation. In practice, from about 0.1 molar proportion of a sulfonyl chloride to about 5 molar proportions, based on the amount of hydroxyl moieties in the polymeric alcohol coating the core support, is used in the practice of this invention. As the proportion of hydroxylic groups converted to sulfonate groups increases, it follows that the loading of biologically active protein subsequently immobilized also increases. Whether such an increase in loading is desirable depends, in part, on the size of the enzyme or other biologically active protein which is immobilized. In particular, as the size of the protein increases greater loading interferes with the expressed activity of the biologically active protein. Consequently, the relative amount of sulfonate esters formed on the cross-linked resin will depend upon the use to which the support matrix will be put, and the optimum may have to be experimentally determined depending upon the biologically active protein immobilized and the process in which it is utilized.

This completes the preparation of the support matrix which can then be conveniently stored, e.g., in 1 millimolar hydrochloric acid at 5° C., prior to immobilization of a biologically active material. This support matrix may be used to immobilize, via a covalent bond, any biologically active material with a primary amino group, which in practice means any biologically active protein, and may also be useful in immobilization via covalent bond formation with a sulfhydryl group. Enzymes, antibodies, and those antigens which are proteins generally can be immobilized on a support matrix of this invention. Examples of enzymes which may be used, which are to be clearly understood as illustrative rather than exhaustive, include glucose isomerase, glucoamylase, lactase, cellulase, glucose oxidase, peroxidase, ribonuclease, urease, histidase, trypsin, papain, hexokinase, chymotrypsin, acylase, invertase, ficin, lysozyme, protease, pepsin, rennin, xylanase, beta amylase, gamma amylase, asparaginase, cholesterol oxidase, alcohol dehydrogenase, amino acid oxidase, collagenase, arginase, catalase, deoxyribonuclease, heparinase, uricase, glutaminase, bilirubin oxidase, B-glucuronidase, phenylalanine ammonia lyase, arginase, UDP glucuroIynyl transferase, streptokinase, tyrosinase, alphagalactosidase, urokinase, superoxide dismutase, fibrinolysin and carboxypeptidase G-1, etc. Antibodies which may be immobilized include both monoclonal and polyclonal antibodies. Illustrative and non-exhaustive examples of antibodies are types $I_gA$, $I_gD$, $I_gE$, $I_gM$, and $I_gG$ immunoglobulin and $F_{ab}$ fragments. Immobilization of the biologically active protein to the support matrix generally occurs readily merely by mixing the support matrix with the biologically active material at, or frequently below, room temperature and at a pH near 7. Because a sulfonic acid is released during the substitution of the biologically active protein for the sulfonate ester, a weak base may be present during immobilization to neutralize the sulfonic acid formed. However, this is not an indispensable requirement, and adequate immobilization usually results merely from shaking the support matrix with a solution of the biologically active protein at a pH from about 5 to about 9 for a time between about 10 minutes and about 72 hours at a temperature between about 5° and about 35° C. The immobilized biologically active material is then recovered simply by separating the solid and washing it well with water or a saline solution to remove adhering but unbound biologically active material.

The following examples are illustrative of our invention which is not to be limited thereto.

EXAMPLE I

Preparation of a finished support matrix. The core support used in this example was a carbonaceous pyropolymer from benzene deposited on a gamma alumina with an approximate surface area of 150 m²/g. The surface area and pore volume characteristics of such a core support are summarized below. Pore volume data were obtained by mercury intrusion.

TABLE 1

| Core Support Characteristics | |
|---|---|
| Total Surface Area | 129 m²/g |
| surface area, >300 Angstrom pore | 71 m²/g |
| surface area, >1000 Angstrom pores | 9.7 m²/g |
| Average pore diameter | 450 Angstroms |
| Total pore volume | 1.45 ml/g |
| pore volume, >300 Angstrom pores | 1.27 ml/g |
| pore volume, >1000 Angstrom pores | 0.29 ml/g |

Similarly finished support matrices may be prepared using titania microspheres as a core support. In this example polyvinyl alcohol will be used to illustrate polymer alcohols generally, 1,4-butenediol diglycidyl ether (BDDE) will exemplify the cross-linking agent, and the 2,2,2-trifluoroethanesulfonate is used as the illustrative sulfonate.

Polyvinyl alcohol (88% hydrolyzed, 96,000 molecular weight) was cast onto the prewashed core support from a 5% solution in 50% ethanol/water in an amount of 20 mL solution per gram of dry core support. After degassing and allowing the mixture to stand overnight, solid was removed by filtration and washed with 10 mL/g ethanol followed by 100 mL/g water and vacuum-air dried. This procedure yielded about 7.5–9.5 weight percent polyvinyl alcohol as a coating.

Cross-linking of the PVA coated on the carbonaceous pyropolymer core support was effected as follows. To the dry PVA coated support was added a solution of NaOH and 2.5 mg/ml $NaBH_4$ in 40% ethanol in a ratio of 1 g support per 7 ml solution and the mixture was degassed. After about 1 minute, 0.18 ml of 95% BDDE per gram of support was slowly added to the mixture with swirling (ca. 13.4 mmol BDDE per gram of PVA or 0.59 mmol BDDE per mol of PVA OH groups). The mixture remained at 50° C. for 6 hours with periodic shaking after which the solid was removed by filtration and washed extensively with water and mild acid to neutrality. Determination of the weight percent polymer by Leco carbon analysis showed approximately the same weight percent polymer as before cross-linking.

A sample of the cross-linked alcohol on the carbonaceous pyropolymer core support was dehydrated by washing with anhydrous acetone. To a mixture of the cross-linked alcohol on the core support in anhydrous acetone (10 mL/g) was added pyridine (1.6 mL/g) and 440 microliters/g of 2,2,2-trifluoroethanesulfonyl chloride was added below the surface of the fluid while swirling. The solution was gently shaken at room temperature for 30 minutes, decanted and washed sequentially with acetone, then with solutions of the following ratios of acetone to 5 mM HCl; (75:25 v/v), (50:50 v/v) and (25:75 v/v). Finally, the activated support (support matrix) was washed with 1 mM hydrochloric acid and stored in the same medium at 4° C. until use.

EXAMPLE II

Immobilization of glucose isomerase. The desired amount of activated support was washed with a 50 mM borate buffer at pH 8.0 containing magnesium sulfate at the same 50 mM concentration. Buffer was decanted, and to the washed activated support was added a solution of glucose isomerase diluted to a concentration of approximately 7 milligram total protein per ml solution, with 5 ml of the solution added per 0.5 grams of support. The mixture was gently agitated for 16 hours at 4° C. and excess liquid was decanted. Solid was thoroughly washed with a 50 mM borate buffer, pH 8.0, to remove adhering but unbound protein, and the amount of immobilized protein was determined by subtracting the amount in the wash from the offered amount. The solid was assayed for immobilized protein by packing a column with the immobilized GI and passing a feedstock of fructose through the column at 2–3 ml/hr at 60° C. The feedstock contained 45% by weight fructose, 50 mM $MgSO_4$ and 50 mM Tris buffer (Tris [hydroxy methyl] amino methane hydrochloride) at pH 8.0 and was saturated with nitrogen. Glucose was measured on a glucose analyzer and the activity of immobilized GI, in units per gram, was calculated according to the formula, $$\text{Activity (U/gm)} = \left( \frac{G - G_o}{100} \right) \frac{(F)}{W} (5.56)$$

where: 1 unit GI leads to 1 micromole glucose formation per minute;

G is glucose concentration measured (in mg/dl);

$G_o$ is background glucose concentration;

F is feedstock flowrate in ml/min;

W is weight of support material in grams

Typically, using 2.5% polyvinyl alcohol of molecular weight 10,000 to coat the core support, there was no adsorbed GI and the amount of immobilized GI varied from 280/400 U/G (16–26 mg/g).

EXAMPLE III

Antibody leach test. The $^{125}$I-I$_g$G leach test was performed as follows. One gram of support was sterilized. Under sterile conditions 20 mg of $^{125}$I-I$_g$G (goat anti-rat diluted with sheep I$_g$G) was offered to the support in PBS at 0.4 mg/mL, approximately 6 cpm/ng I$_g$G, and the protein was immobilized on a periodic shaker at 4° C. for 2–7 days. The column was poured with the offering solution and washed twice with a phosphate buffered saline solution, 0.02M phosphate and 0.15M NaCl, pH 7.0 (PBS). The effluent was collected and the I$_g$G content of the solution was determined by counting an aliquot with the Micromedics Gamma Counter and calculated from the current specific activity of the offering solution. The loading of the I$_g$G in the column was the difference between the offering and the wash solutions. The column was set up to maintain sterility and each buffer was pumped through the column at 3 LHSV. Small initial fractions were collected to determine the peak of eluted I$_g$G. Larger fractions were taken until the effluent had <200 ppb of $^{125}$I-I$_g$G. The total amount of I$_g$G eluted was determined by counting an aliquot of the entire eluant of a single buffer, multiplying by the total eluant volume, and dividing by the current specific activity of the offering solution. Results are summarized in Tables 2 and 3 which compare our immobilization system with a commercial support, Eupergit C purchased from Rohm Pharma GmbH, Weiterstadt, Germany.

TABLE 2

$^{125}$I-IgG LEACH TEST

| Buffer | Peak (μg/mL) | Total IgG Loss (μg) | % Loss |
|---|---|---|---|
| 1. PBS #1 | 0.665 (±2%) | 594 (±3%) | 5.5 (±4%) |
| 2. 2M NaCl | 0.437 | 265 | 2.8 |
| 3. PBS #2 | 0.125 | 61 | 0.7 |
| 4. pH 2.5 | 0.310 | 59 | 0.7 |
| 5. PBS #3 | 3.60 | 229 | 2.5 |
| 6. pH1 | 1.82 | 249 | 2.8 |
| 7. PBS #4 | 0.130 | 40 | 0.5 |
| Stat (4 days) | 5.58 | 28 | 0.4 |
| | | Total | 15.9% |

IgG Immobilized = 10.0 mg/g

TABLE 3

$^{125}$I-IgG LEACH TEST (EUPERGIT C)

| Buffer | Peak (μg/mL) | Total IgG Loss (μg) | % Loss |
|---|---|---|---|
| 1. PBS #1 | 5.13 (±2%) | 632 (±3%) | 3.2 (±4%) |
| 2. 2M NaCl | 1.16 | 1240 | 7.0 |
| 3. PBS #2 | 0.234 | 213 | 1.2 |
| Stat (5 days) | 3.69 | 11 | |
| 4. pH 2.5 | 1.49 | 354 | 2.4 |
| 5. PBS #3 | 0.840 | 50 | 0.3 |
| 6. pH 11 | 6.38 | 1770 | 11.0 |
| | | Total | 29.6% |

IgG Immobilized = 18.6 mg/g

Our support matrix leaches 80% less net $^{125}$I-I$_g$G than Eupergit C in 2M NaCl and 85% less net I$_g$G at pH 11. Although out immobilized system appers to leach less net I$_g$G at pH 2.5, the following PBS wash indicates that liberated $^{125}$I may be adhering to the column at pH 2.5 and eluting when the pH is raised to 7. If this is in fact the case, our system is at least comparable to the commercial one. The $^{125}$I-I$_g$G test is typical of the test run on supports to determine suitability under contemplated field conditions.

EXAMPLE IV

Non-specific protein adsorption; leaching of polymer and cross-linked polymer. The type of polymer coating most suitable for specific protein immobilization was determined by measuring non-specific adsorption of BSA onto each composite. Adsorption must be eliminated since adsorbed protein will contaminate the eluted antigen product from the immunoaffinity column. The results are shown in Table 4. Polyvinyl alcohol with 88% of the hydroxyls in the free form prevented protein adsorption to the Kocite and was used in subsequent experiments.

TABLE 4

Effect of Polymer Coating on Non-Specific Adsorption.

| MATERIAL | NON-SPECIFIC PROTEIN ADSORPTION (MG/G) |
|---|---|
| Core Support[a] | 100 ± 10 |
| + Cellulose Triacetate | 78 |
| + Cellulose Acetate-Butyrate | 40 |
| + Cellulose Propionate | 30 ± 10 |
| + Polyvinyl Alcohol (88% Hy.) | 0 |

[a]Carbonaceous pyropolymer on gamma alumina.

The cross-linking conditions for the PVA coating were determined by timing the gelling reaction of a 1% PVA (molecular weight 96,000) solution at BDDE:PVA ratios of 0.1 to 13.0 mmol:gram of PVA and at 23°, 37° and 60° C. The reaction at 37° C., 24 hours, BDDE:PVA ratio of 13:1 gave the smoothest, most complete gel.

PVA must be cross-linked to prevent dissolution of the polymer since PVA is water soluble and its leach will remove immobilized protein. In fact, the leach of the polymer must be very low. The stability of the PVA coating toward 2M NaCl, 50 mM phosphate pH 2 and 50 mM phosphate pH 11 was examined by eluting 10 cc of cross-linked PVA on a carbonaceous pyropolymer core support at 3 LHSV with the various buffers and measuring carbon leach. Less than 200 ppm (detection limit) of carbon was eluted. Another test for PVA leach was conducted by reacting methyl pyridinium activated, cross-linked PVA on a carbonaceous pyropolymer core support with $^{14}$C-ethylenediamine followed by elution with the above buffers. Peak fractions of $^{14}$C eluted from the PVA-Kocite column were run over a Sephadex ™ G15 gel filtration column to separate labeled polymer from free ethylenediamine. Noncrosslinked material showed leach of PVA but cross-linked polymer did not. This test could detect >230 ppm polyvinyl alcohol in the original column leachate.

EXAMPLE V

Effect of amount of polymer coating support. Polyvinyl alcohol of 10,000 molecular weight, 88% hydrolyzed, was cast from 50% ethanol onto a core support of a carbonaceous pyropolymer on gamma alumina and subsequently cross-linked and converted to the trifluoroethanesulfonate as described in Example I. The supports were contacted with solutions of glucose isomerase as described in Example II. Results are summarized in accompanying Table 5.

TABLE 5

Effect of Amount of Polymer Coating.

| % PVA Solution coated from wt/vol | % Polymer on support (wt) | Adsorbed GI mg/g | Adsorbed GI U/g | Immobilized GI (TC) mg/g | Immobilized GI (TC) U/g | Spec. act.[b] U/mg |
|---|---|---|---|---|---|---|
| 0   | 0.6 ± 0.8 | 60 ± 2 | 122 | 60 ± 2 | 188 | 3 |
| 0.1 | 4.2       | 34     | —[a] | —[a]  | —[a] | —[a] |
| 0.5 | 6.4       | 17     | —   | —     | —    | —  |
| 1.0 | 7.2       | 4      | 16  | 24    | 384  | 16 ± 1.5 |
| 2.5 | 9.2       | 0      | 0   | 16    | 279  | 17 |
| 5.0 | 10.0      | 0      | 0   | 17    | 207  | 12 |

[a]Not Determined
[b]Units of immobilized GI per mg immobilized protein.

These data seam to support the conclusion that at least for polvinyl alcohol non-specific adsorption becomes vanishingly small when the coating is present at levels greater than about 7%.

EXAMPLE VI

Effect of molecular weight on PVA coatings. Polyvinyl alcohol which was 88% hydrolyzed was used as a 2.5% solution in 50% aqueous alcohol and cast onto a core support of a carbonaceous pyropolymer on alumina. A finished support matrix was prepared from each sample as previously described, and the various support matrices were tested for the amount of glucose isomerase adsorbed and the amount immobilized. These data are summarized in Table 6

TABLE 6

Effect of Molecular Weight of Polyvinyl Alcohol on Support Properties.

| Mol Wt. | % Polymer on Support | Adsorbed GI Mg/g | Adsorbed GI U/g | Adsorbed GI Spec. Act U/mg | Immobilized GI (TC) Mg/g | Immobilized GI (TC) U/g | Immobilized GI (TC) Spec. Act. U/mg |
|---|---|---|---|---|---|---|---|
| 2,000  | 8.8  | 0 ± 2 | 0   | — | 38 ± 2 | 530 ± 51 | 14 |
| 10,000 | 10.0 | 0     | 0   | — | 26     | 398      | 15 |
| 25,000 | 9.6  | 1.8   | 0   | — | 23     | 392      | 17 |
| 78,000 | 7.8  | 16    | 79  | 5 | 37     | 432      | 10 |
| 96,000 | 8.2  | 20    | 105 | 5 | 34     | 310      | 10 |

These data indicate that there is no or little non-specific adsorption when using polyvinyl alcohol up to a molecular weight of about 25,000. Maximum loading of immobilized GI appears to occur with the lowest molecular weight tested, although there appears to be relatively little change in the range between about 2,000 and 78,000 molecular weight. Specific activity of immobilized GI remains relatively high and constant up to a molecular weight of 25,000, then drops due to adsorbed and less active protein. In analogous experiments, there appeared to be no impor;tant differences between 88 and 96% hydrolyzed polyvinyl alcohol.

EXAMPLE VII

Leaching of core support. Samples of a carbonaceous pyropolymer on gamma alumina were heated at 400° C. for 3½ hours under a nitrogen stream, washed with water and packed in a 10 cc bed. The column was then eluted with 1M phosphate buffer, pH 7, at 3 LHSV. Fractions of eluate were analyzed for UV absorbing material at 214 millimicrons ($A_{214}$) and for carbon. The results were compared with a column that had not been heat treated.

Eluate from untreated material showed strong absorbtion at $A_{214}$ for the first 3.4 bed volumes which then went to zero. Heated material, however, showed no absorbing material leaching from the column. Peak adsorbing fractions of eluate from unheated material, corresponding fractions from heated material, and phosphate buffer were analyzed for carbon.

| Material | ppm Carbon |
|---|---|
| Unheated | 2.9 |
| Heated   | 2.6 |
| Buffer   | 1.2 |

Therefore, aromatic leach (uv absorbing material) can be eliminated by a preheating step. The peak of carbon leach does not change much with heating but is only 1.4–1.7 ppm.

Samples of carbonaceous pyropolymer on alumina were prepared with different carbon content and from various carbon sources. A packed bed of these materials, as well as one of titania microspheres and of gamma alumina run as a reference, were eluted with 30 bed volumes of 1M phosphate buffer, pH 7, at 3 LHSV. The eluate was analyzed for aluminum or titanium with results tabulated below.

TABLE 7

Metals Leach from Core Supports.

| Support | Percent Carbon | Carbon Source | ppm metal in leachate |
|---|---|---|---|
| Carbonaceous pyropolymer | 17 | benzene | 2.4 Al |
| Carbonaceous pyropolymer | 38 | benzene | 1.7 Al |
| Carbonaceous pyropolymer | 30 | glucose | <0.1 Al |
| Gamma alumina |  |  | 20 Al |
| Titania |  |  | <0.1 Ti |

What is claimed is:

1. A method of making a support matrix for immobilization of biologically active proteins comprising coating with a polymeric alcohol a core support which is titania, titanated alumina, or a carbonaceous pyropolymer possessing recurring units containing at least carbon and hydrogen atoms deposited on a high surface area inorganic oxide, cross-linking the polymeric alcohol by reacting it with an hydroxyl-reactive cross-linking agent which is in a molar excess relative to the molar proportion of said polymeric alcohol, converting a portion of the hydroxyl groups of the cross-linked alcohol to a sulfonate ester and recovering the resulting support matrix.

2. The method of claim 1 where the core support is titania.

3. The method of claim 1 where the core support is a carbonaceous pyropolymer deposited on an inorganic oxide selected from the group consisting of alumina, silica-alumina, silica-zirconia, silica, controlled pore glass, hydroxyapatite, zirconia-titania, and alumina-zirconia.

4. The method of claim 3 where the inorganic oxide is alumina.

5. The method of claim 1 where the polymeric alcohol is selected from the group consisting of polyvinyl alcohol, agarose, and cellulose esters containing free hydroxyl groups.

6. The method of claim 5 where the alcohol is polyvinyl alcohol.

7. The method of claim 5 where the polyvinyl alcohol has a molecular weight in the range between about 2,000 and about 25,000.

8. The method of claim 1 where the core support is coated with at least 3% by weight of polyvinyl alcohol.

9. The method of claim 8 where the core support is coated with from about 7 to about 15 weight percent polyvinyl alcohol.

10. The method of claim 1 where the cross-linking agent is selected from: a diglycidyl ether of formula

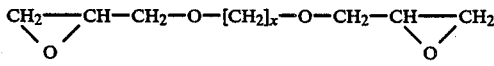

where x is an integer from 1 to about 10; epichlorohydrin; aliphatic diisocyanates of the formula $OCN(CH_2)_yNCO$ where y is an integer from 2 to about 10; benzene diisocyanate; toluene diisocyanate; and divinylsulfone.

11. The method of claim 10 where the cross-linking agent is a diglycidyl ether and x is from 2 through about 6.

12. The method of claim 10 where the cross-linking agent is an aliphatic diisocyanate where y is from 4 through about 8.

13. The method of claim 1 where the sulfonate ester is selected from the group consisting of trifluoroethanesulfonate, trifluoromethanesulfonate, para-toluenesulfonate, para-bromobenzenesulfonate, para-nitrobenzenesulfonate, and 2,4-dinitrobenzenesulfonate.

14. The method of claim 1 further characterized in that the sulfonate ester is formed by the reaction with from about 0.1 to about 5.0 molar proportions, based on the hydroxyl moieties in the polymeric alcohol coating, of an activated sulfonic acid with the cross-linked polymeric alcohol.

15. A support matrix resulting from the method of claim 1.

16. An immobilized biologically active protein system having covalently bound biologically active protein resulting from nucleophilic displacement of sulfonate ester groups of the support matrix of claim 15 by a primary amino or sulfhydryl moiety of said protein.

17. The immobilized biologically active protein system of claim 16 where the protein is an enzyme, an antibody, or an antigen.

18. The immobilized biologically active protein system of claim 17 where the protein is an enzyme selected from the group consisting of glucose isomerase, glucoamylase, lactase, cellulase, glucose oxidase, peroxidase, ribonuclease, urease, histidase, trypsin, papain, hexakinase, chymotrypsin, acylase, invertase, ficin, lysozyme, protease, pepsin, rennin, xylanase, beta amylase, gamma amylase, asparaginase, cholesterol oxidase, alcohol dehydrogenase, amino acid oxidase, collagenase, arginase, catalase, deoxyribonuclease, heparinase, uricase, glutaminase, bilirubin oxidase, B-glucuronidase, phenylalanine ammonia lyase, arginase, UDP glucurolnyl transferase, streptokinase, tyrosinase, alpha-galactosidase, urokinase, superoxide dismutase, fibrinolysin and carboxypeptidase G-1.

19. The immobilized biologically active protein system of claim 17 where the protein is an antibody selected from the group consisting of $I_gA$, $I_gE$, $I_gM$, $I_gD$ and $I_gG$ immunoglobulins and $F_{ab}$ fragments.

* * * * *